(12) United States Patent  
Rathjen

(10) Patent No.: US 9,170,170 B2  
(45) Date of Patent: Oct. 27, 2015

(54) DEVICE AND METHOD FOR DETERMINING THE FOCUS POSITION OF A LASER BEAM

(71) Applicant: ZIEMER OPHTHALMIC SYSTEMS AG, Port (CH)

(72) Inventor: Christian Rathjen, Bremen (DE)

(73) Assignee: ZIEMER OPHTHALMIC SYSTEMS AG (CH)

( * ) Notice: Subject to any disclaimer, the term of this patent is extended or adjusted under 35 U.S.C. 154(b) by 0 days.

(21) Appl. No.: 13/722,604

(22) Filed: Dec. 20, 2012

(65) Prior Publication Data

US 2014/0104600 A1  Apr. 17, 2014

Related U.S. Application Data

(60) Provisional application No. 61/579,369, filed on Dec. 22, 2011.

(51) Int. Cl.
| | |
|---|---|
| G01M 11/02 | (2006.01) |
| B23K 26/00 | (2014.01) |
| B23K 26/04 | (2014.01) |
| B23K 26/06 | (2014.01) |
| B23K 26/08 | (2014.01) |

(Continued)

(52) U.S. Cl.
CPC ............... *G01M 11/02* (2013.01); *A61F 9/009* (2013.01); *A61F 9/00825* (2013.01); *B23K 26/0027* (2013.01); *B23K 26/041* (2013.01); *B23K 26/0635* (2013.01); *B23K 26/0815* (2013.01); *A61F 2009/0087* (2013.01); *A61F 2009/00844* (2013.01); *A61F 2009/00872* (2013.01); *A61F 2009/00897* (2013.01)

(58) Field of Classification Search
CPC ...... A61F 9/008; G01S 5/163; G03F 7/70358; G01C 3/32; G01C 25/005; G01B 11/14; G01B 11/26; G01B 9/02063
USPC .................. 356/399–401, 614–623, 121–127, 356/234.1, 243.4, 243.8; 606/4, 5, 12
See application file for complete search history.

(56) References Cited

U.S. PATENT DOCUMENTS

| | | | | |
|---|---|---|---|---|
| 5,267,012 | A | * | 11/1993 | Sasnett et al. .................. 356/121 |
| 5,772,656 | A | * | 6/1998 | Klopotek .......................... 606/12 |
| 5,909,274 | A | * | 6/1999 | Stucchi ........................... 356/121 |

(Continued)

FOREIGN PATENT DOCUMENTS

| | | |
|---|---|---|
| DE | 103 49 296 A1 | 5/2005 |
| EP | 1 034 755 A1 | 9/2000 |
| EP | 2 069 099 | 7/2011 |

*Primary Examiner* — Hoa Pham  
(74) *Attorney, Agent, or Firm* — Ostrolenk Faber LLP

(57) ABSTRACT

In order to determine the focus position of a laser beam (60, 60a) in an ophthalmological laser projection system (1), at least one measurement marking (3) applied to a reference area (20) is passed over by means of the laser beam (60, 60a) along a scanning path. A measurement signal created by passing over the measurement marking (3) is captured. Time values from at least one signal edge created in the measurement signal when passing over edges of the measurement marking (3) are determined and the focus position is established on the basis of the time values. By scanning defined measurement markings (3) and establishing time values of signal edges created when edges of the measurement marking (3) are passed over, it is possible to determine the focus position of the laser beam (60, 60a) without focusing movements being required for this during the measurement.

12 Claims, 3 Drawing Sheets

(51) Int. Cl.
*A61F 9/008* (2006.01)
*A61F 9/009* (2006.01)

(56) References Cited

U.S. PATENT DOCUMENTS

| | | | |
|---|---|---|---|
| 6,151,109 A * | 11/2000 | Bromssen et al. | 356/121 |
| 6,210,401 B1 * | 4/2001 | Lai | 606/12 |
| 6,559,934 B1 * | 5/2003 | Yee et al. | 356/121 |
| 7,180,607 B2 * | 2/2007 | Kyle et al. | 356/614 |
| 7,652,761 B2 * | 1/2010 | Somani et al. | 356/243.1 |
| 7,846,152 B2 * | 12/2010 | Chernyak et al. | 606/10 |
| 8,088,124 B2 * | 1/2012 | Loesel et al. | 606/10 |
| 8,289,384 B2 * | 10/2012 | Kojima | 348/80 |
| 2002/0120198 A1 * | 8/2002 | Nakamura | 600/473 |
| 2004/0070761 A1 | 4/2004 | Horvath et al. | |
| 2005/0215986 A1 * | 9/2005 | Chernyak et al. | 606/5 |
| 2007/0091264 A1 * | 4/2007 | Kahlen | 351/206 |
| 2013/0150837 A1 * | 6/2013 | Rathjen et al. | 606/4 |
| 2014/0200562 A1 * | 7/2014 | Rathjen | 606/4 |

* cited by examiner

DEVICE AND METHOD FOR DETERMINING THE FOCUS POSITION OF A LASER BEAM

CROSS-REFERENCE TO RELATED APPLICATIONS

The present application claims benefit of and priority to U.S. Provisional Patent Application Ser. No. 61/579,369 entitled VORRICHTUNG UND VERFAHREN ZUM BESTIMMEN DER FOKUSPOSITION EINES LASER-STRAHLS filed Dec. 22, 2011, the entire content of which is hereby incorporated by reference herein.

BACKGROUND

1. Field of the Disclosure

The present invention relates to a device and a method for determining the focus position of a laser beam in an ophthalmological laser projection system. The present invention more particularly relates to a device and a method for determining the focus position in the projection direction of the laser beam.

2. Related Art

In ophthalmology, pulsed laser beams, for example laser pulses with a pulse duration in the femtosecond range (1 fs=$10^{-15}$ s), are used for treating eye tissue. In the process, incisions are carried out by focused projection of the laser pulses into the eye tissue. As a result of production tolerances and/or thermal expansions during the production and operation of ophthalmological laser projection systems, the precise focus position of the laser pulses in the projection direction is generally not known with a sufficiently high accuracy with respect to the ophthalmological laser projection system, more particularly with respect to the projection lens and/or a contact body through which the laser pulses are projected into the tissue. Even if the focus position can be determined by calibration during the production of the laser projection system, it is possible for this position to change during operation, for example in the case of thermal material expansions or when replacing the utilized contact body.

EP 2 069 099 describes a method for confocal detection of the entry surface and exit surface of a contact body. As per EP 2 069 099, a laser measurement beam is preferably focused onto the surface by means of a variable focus adjustment apparatus and returned or reflected radiation is detected confocally. The position of the surfaces is determined from the confocally detected radiation and the associated setting of the variable focus adjustment apparatus. The method as per EP 2 069 099 requires a focusing movement for determining the surfaces, which can adversely affect the measurement accuracy. Moreover, the confocal detection supplies very weak signals, and therefore much metrological effort is required for accurate measurements.

SUMMARY

It is an object of the present invention to propose a device and a method for determining the focus position of a laser beam in an ophthalmological laser projection system, which, at the very least, do not have some of the disadvantages of known systems. In particular, it is an object of the present invention to propose a device and a method for determining the focus position in the projection direction of the laser beam, which make do without focusing movements during the measurement procedure.

According to the present invention, these objects are achieved by the features of the independent claims. Moreover, further advantageous embodiments emerge from the dependent claims and the description.

The aforementioned objects are more particularly achieved by the present invention by virtue of the fact that, in order to determine the focus position of a laser beam in an ophthalmological laser projection system, at least one measurement marking applied to a reference area, more particularly a reference plane, is passed over by means of the laser beam along a scanning path, that a measurement signal created by passing over the measurement marking is captured, that time values of at least one signal edge created in the measurement signal when passing over edges of the measurement marking are determined, and that the focus position is determined on the basis of the time values. By scanning defined measurement markings and establishing time values of signal edges created when passing over edges of the measurement marking, it is possible to determine the focus position of the laser beam without this requiring focusing movements during the measurement.

In one embodiment variant, the measurement marking has a photoactive design and the measurement marking creates the measurement signal when the laser beam passes over the measurement marking. In an alternative embodiment variant, the measurement marking has a reflecting design and the measurement signal is created as a result of a laser beam which is reflected when the measurement marking is passed over. In a further alternative embodiment variant, the measurement marking has an absorbing design and the measurement signal is created as a result of a laser beam which is absorbed or not reflected or not transmitted when the measurement marking is passed over.

In one embodiment variant, the beam width is determined on the basis of the time values and the focus position in the projection direction of the laser beam is established on the basis of the beam width.

In one embodiment variant, a time duration between an upper and a lower signal threshold is determined in the signal edge, the beam width is determined on the basis of the time duration, and the focus position in the projection direction of the laser beam is established on the basis of the beam width.

In one embodiment variant, the measurement marking is designed with a gap or bar having a known width. The gap or bar is passed over on a scanning path running across the gap or bar. A time duration for passing over the width of the gap or bar is determined from the measurement signal and the focus position is established on the basis of this time duration and the width of the gap or bar. In the case of a measurement marking with a gap or bar, two edges with a known distance are successively passed over such that the current speed at which the measurement marking is scanned can be determined. This therefore also makes it possible to determine the focus position if the scanning speed is variable and unknown. The closer the edges or signal edges created thereby are together, the more precise the measurement is even in the case of a variable scanning speed.

In a further embodiment variant, a plurality of measurement markings on the reference area are arranged in a circle. The measurement markings are respectively designed with at least one first edge running substantially perpendicular to the circle and a second edge running obliquely to this first edge. The circularly arranged measurement markings are passed over on a circular or spiral scanning path. Time values are determined from the signal edges created in the measurement signal when passing over the first edge and the second edge and a centering characteristic with respect to the centering of the circular or spiral scanning path with respect to the circularly arranged measurement markings is established from the time values.

BRIEF DESCRIPTION OF THE DRAWINGS

An embodiment of the present invention is described below on the basis of an example. The exemplary embodiment is illustrated by the following attached figures.

DETAILED DESCRIPTION OF THE EMBODIMENTS

Figure 1:
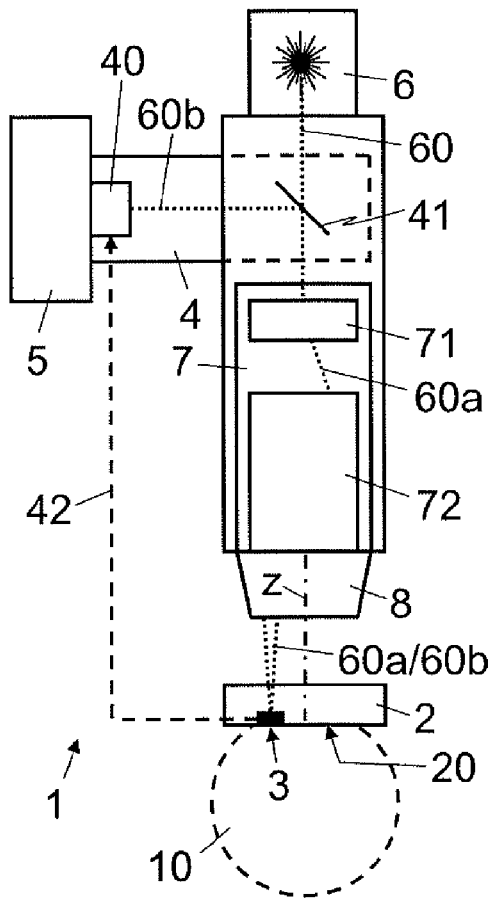
FIG. 1: shows a block diagram, which schematically illustrates an ophthalmological laser projection system with a device for determining the focus position of the laser beam.

In FIG. 1, reference sign 1 relates to an ophthalmological laser system with a laser source 6 for generating a laser beam 60. The laser source 6 is designed to generate a pulsed laser beam 60, more particularly femtosecond laser pulses (1 fs=$10^{-15}$ s). The laser beam 60 is transmitted to the projection optical unit 8 from the laser source 6 via an optical transmission system 7, where said projection optical unit is designed to project the laser beam 60 or the laser pulses thereof in a focused manner into the eye tissue 10, for example into the cornea or the lens of the eye, etc. In addition to optical elements 72 such as lenses and mirrors, the optical transmission system 7 moreover comprises a beam-deflecting scanner 71. For the purposes of deflecting the laser beam 60, the scanner 71 preferably comprises a moveable mirror and is, for example, embodied as a galvano scanner, piezo scanner, polygon scanner or resonance scanner. The deflected laser beam 60a is projected onto or into the eye tissue 10 via the optical elements 72 of the transmission system 7 and the projection optical unit 8, and moved along a defined scanning path by means of the scanner 71. In an alternative variant, the scanner 71 comprises one or more drives for mechanically moving the projection optical unit 8 or parts of the projection optical unit 8.

In order to determine the focus position of the laser beam 60, provision is made for a device 10 (see also FIG. 2) which has one or more measurement markings 3, 3a, 3b, 3c, 3d (see also FIG. 3), which are arranged on a reference area 20, more particularly on a reference plane, of a body 2.

Figure 2:
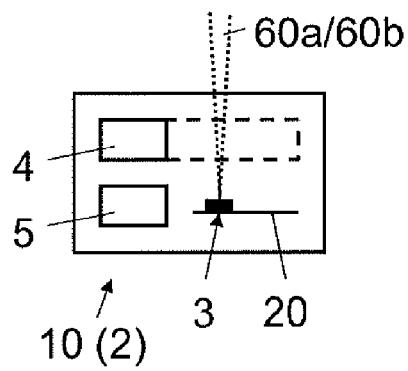
FIG. 2: shows a block diagram, which schematically illustrates the device for determining the focus position of the laser beam.

As illustrated schematically in FIG. 2, the device 10 for determining the focus position of the laser beam 60 moreover comprises a detection system 4 and, connected thereto, a processing system 5.

As illustrated schematically in FIG. 1, the body 2 is, in one variant, embodied as a transparent or semitransparent contact body which, by means of e.g. a suction ring, is attached to the eye during the treatment of the eye tissue 10. In an alternative variant, the body 2 is placed in front of the eye without touching the latter, said body for example being fixed in the beam path or it being possible for said body to be temporarily inserted, slid or pivoted into the beam path. Depending on the embodiment variant, the measurement markings 3, 3a, 3b, 3c, 3d are arranged on a reference area 20, which is arranged on a surface of the body 2 facing the eye, on a surface of the body 2 facing away from the eye or within the body 2, preferably perpendicular to the projection axis z of the projection optical unit 8. In a further embodiment variant, the body 2 is embodied as an artificial eye, i.e. it is designed in the form of a human eye.

In different embodiment variants, the measurement markings 3, 3a, 3b, 3c, 3d, 3d have a reflecting (or absorbing) or photoactive design. In the reflecting variant, a laser beam 60a projected onto the measurement marking 3, 3a, 3b, 3c, 3d is reflected by the measurement marking 3, 3a, 3b, 3c, 3d. The reflected laser beam 60b is captured by the detection system 4, for example via a deflection mirror 41, fed to a signal converter 40 and recorded as measurement signal in a data storage unit. Conversely, the detection system 4 detects an absorbed laser beam in the case of an absorbing measurement marking 3, 3a, 3b, 3c, 3d, for example as a result of a missing reflection or transmission of the laser beam 60, 60a. If a missing transmission of the laser beam 60, 60a through the body 2 is detected as a result of an absorbing marking 3, 3a, 3b, 3c, 3d, the detection system 4 captures the transmitted laser beam 60, 60a on the side of the body 2 or reference area 20 facing away from the projection optical unit 8. The signal converter 40 for example comprises a photosensor and an A/D converter. The reflecting measurement markings 3, 3a, 3b, 3c, 3d comprise mirroring and diffusely reflecting materials. By way of example, the reflecting measurement markings 3, 3a, 3b, 3c, 3d are embodied as chrome masks, diaphragms or partly transparent, dichroic coatings. In a further variant, the measurement markings 3, 3a, 3b, 3c, 3d have a wavelength-selective design, and so these let laser beams 60, 60a of a first wavelength pass in transparent fashion for the purpose of treating the eye tissue 10 and reflect or absorb laser beams 60, 60a of a second wavelength for the purpose of determining the focus position. In the photoactive variant, the measurement marking 3, 3a, 3b, 3c, 3d creates a measurement signal as a result of a laser beam 60a being projected thereon, said measurement signal being captured by the detection system 4 and fed to the signal converter 40 via a signal line 42 for the purpose of digitized recording in the data storage unit, as indicated in FIG. 1 by the dashed arrow. By way of example, the photoactive measurement markings 3, 3a, 3b, 3c, 3d are embodied as photosensors for generating a photocurrent or as photoresistors with a light-dependent resistance.

The processing system 5 is designed to establish the focus position of the laser beam 60, 60a on the basis of the captured measurement signal, i.e. to establish the current position of the focus of the laser beam 60, 60a in the projection direction z' or as a relative value on the projection axis z with respect to the projection optical unit 8 or other reference points of the ophthalmological laser system 1. The functionality and functioning of the processing system 5 will be described in more detail below. The processing system 5 is embodied as logic module and, depending on the embodiment variant, comprises a processor and programmed software modules with stored program code for controlling the processor, or programmed hardware logic. A person skilled in the art will understand that the processing system 5 can also be embodied with (electronic) hardware components in a further embodiment variant.

In one embodiment variant, the device 10 for determining the focus position of the laser beam 60 is designed as part of the ophthalmological laser system 1, as illustrated schematically in FIG. 1. In an alternative embodiment variant, the device 10 for determining the focus position of the laser beam 60, 60a is designed in or as a body 2, i.e. the body 2 moreover comprises the detection system 4 and the processing system 5 in addition to the reference area 20 and the measurement markings 3, 3a, 3b, 3c, 3d arranged thereon, as indicated in FIG. 2 by the reference sign 2 between parentheses.

Figure 3:
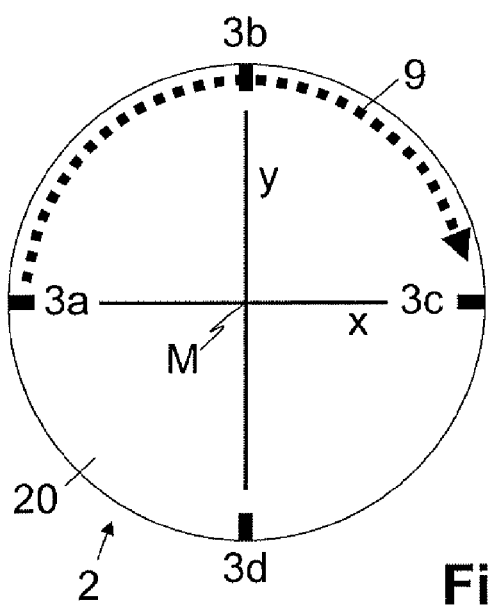
FIG. 3: shows a plan view of an example of a measurement marking (on the right) and an arrangement of a plurality of measurement markings on a reference area of a body (on the left).
Figure 3:
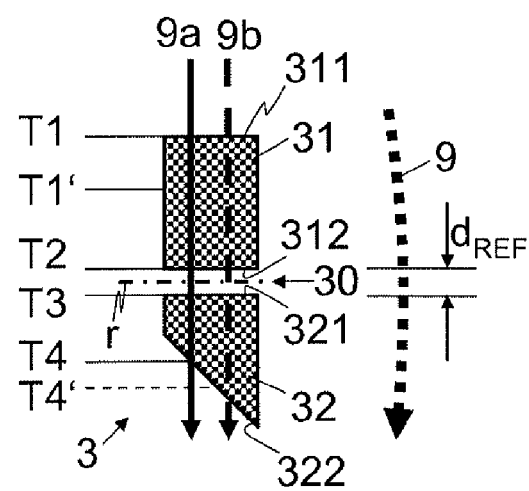

On the right-hand side, FIG. 3 shows an example of a measurement marking 3, which, in the direction of the arrow illustrated, is passed over (scanned) by the laser beam 60, 60a on one or more scanning paths 9a, 9b. As can be seen from FIG. 3, the measurement marking 3 has a gap 30 with a defined width $d_{REF}$, over which the laser beam passes on a scanning path 9, 9a, 9b. By way of example, the width $d_{REF}$ is between 40 μm and 100 μm, for example 60 μm. The gap 30 differs from the remaining part of the measurement marking 3 in that it is not reflecting (or absorbing) or not photoactive. A person skilled in the art will understand that, in an alternative embodiment variant, a bar with a defined width $d_{REF}$ can be provided in place of a gap, which bar is made of the reflecting (or absorbing) or photoactive material. When the gap 30 or a corresponding bar is passed over, the laser beam 60 crosses over two parallel edges 312, 321 of the measurement marking 3, which define or delimit the gap 30 or bar perpendicularly to the scanning path 9, 9a, 9b. At these edges 312, 321, a measurement signal created by passing over the measurement marking 3 respectively has a signal edge with an increasing or decreasing signal value because the measurement marking 3 has a boundary at this point between reflecting and non-reflecting (or absorbing and non-absorbing) or photoactive and non-photoactive material.

In the measurement marking 3 imaged on the right-hand side in FIG. 3, the gap 30 is defined or delimited by an entry region 31 ahead of the gap 30 and an exit region 32 behind the gap 30. The entry region 31 has a rectangular shape with an entry edge 311 and an exit edge 321 delimiting the gap 30, which edges run substantially perpendicular to the scanning path 9, 9a, 9b. The exit region 32 has a right-angled trapezoidal shape with a entry edge 321, which delimits the gap 30 and runs substantially perpendicular to the scanning path 9, 9a, 9b, and an exit edge 322 which runs obliquely, for example at 45°, to the scanning path 9, 9a, 9b. The two side edges of the entry region 31 and of the exit region 32 run perpendicular to the entry edge 311 and exit edge 312 of the entry region 31 and to the entry edge 321 of the exit region 32. The reference signs T1, T1', T2, T3, T4, T4' denote times at which the laser beam 60, 60a passes over or scans a respective edge of the measurement marking 3, 3a, 3b, 3c, 3d.

The following paragraphs will, with reference to FIGS. 4, 5, 6 and 7, describe the functions of the processing system 5 and the method for determining the focus position of the laser beam 60.

During the initiation of the measurement process, the laser source 6 is changed into a measurement mode, in which the power of the laser source 6 is set to a measurement power which does not damage or destroy the measurement markings 3, 3a, 3b, 3c, 3d.

The scanner 71 is actuated such that it scans the reference area 20 along a scanning path 9, 9a, 9b. As illustrated on the left-hand side of FIG. 3, the reference area 20 is swept e.g. by the laser beam 60, 60a on a circular scanning path 9. In the process, the detection system 4 captures the measurement signal s which is amplitude-modulated by the measurement markings 3, 3a, 3b, 3c, 3d either synchronously or asynchronously to sweeping the scanning path 9, 9a, 9b, which measurement signal is based on the signal created on the reference area 20 by the laser beam 60b reflected (or absorbed) by the reflecting (or absorbing) measurement markings 3, 3a, 3b, 3c, 3d or on the signal created by the photoactive measurement markings 3, 3a, 3b, 3c, 3d.

Figure 4:
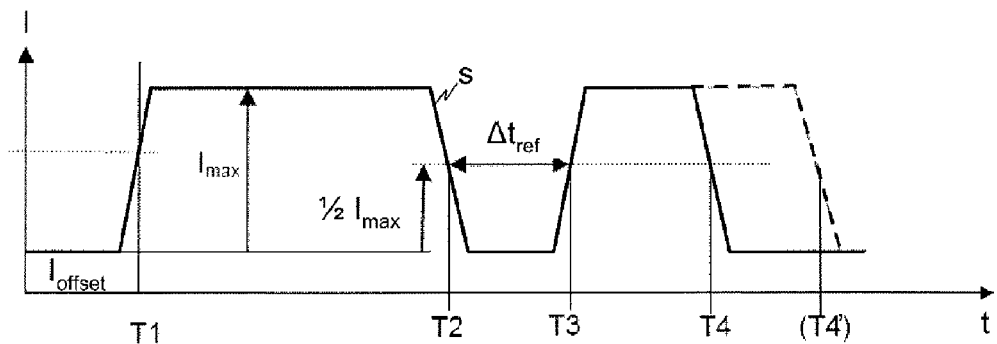
FIG. 4: shows an example of a measurement signal with signal edges which are created when passing over edges of the measurement marking by means of the laser beam.

In a preparing correction phase, the processing system 5 establishes the current dark value, i.e. the signal level which is measured on the reference area 20 in the regions outside of the measurement markings 3, 3a, 3b, 3c, 3d, from the signal profile of the recorded measurement signal s, for example prior to reaching the entry edge 311 at the time T1 (or at the time T1' in the case of an entry region 31 with a different length). This current dark value is, as illustrated in FIG. 4, used as offset value $I_{offset}$ for correcting the measurement signal s by subtracting the offset value $I_{offset}$ from the signal level I. Subsequently, the processing system 5 establishes the mean value of the measurement signal s in a defined region of the measurement marking 3, for example in the entry region 31 between the entry edge 311 and the exit edge 312, in the period of time between the times T1 (T1') and T2, and establishes the maximum level $I_{max}$ of the measurement signal s therefrom and normalizes the measurement signal s with respect to the maximum level $I_{max}$. Here, the processing system 5 sets the thresholds of the signal level for determining the times T1, T1', T2, T3, T4, T4' of passing over a signal edge at an edge of the measurement marking 3, 3a, 3b, 3c, 3d to be half the maximum level $I_{max}$.

Figure 5:
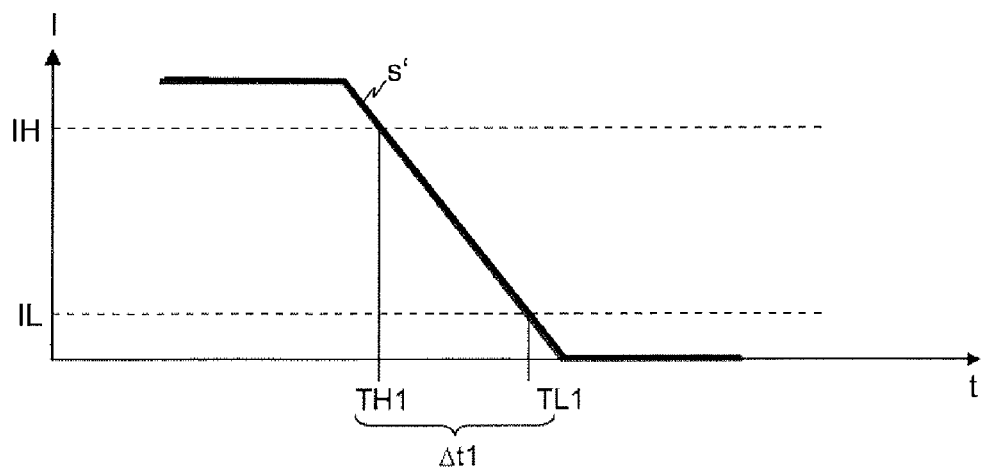
FIG. 5: shows an example of a signal edge of the offset-corrected measurement signal and measurement points at an upper and lower signal threshold for determining time values and a time duration of the signal edge based thereon.
Figure 6:
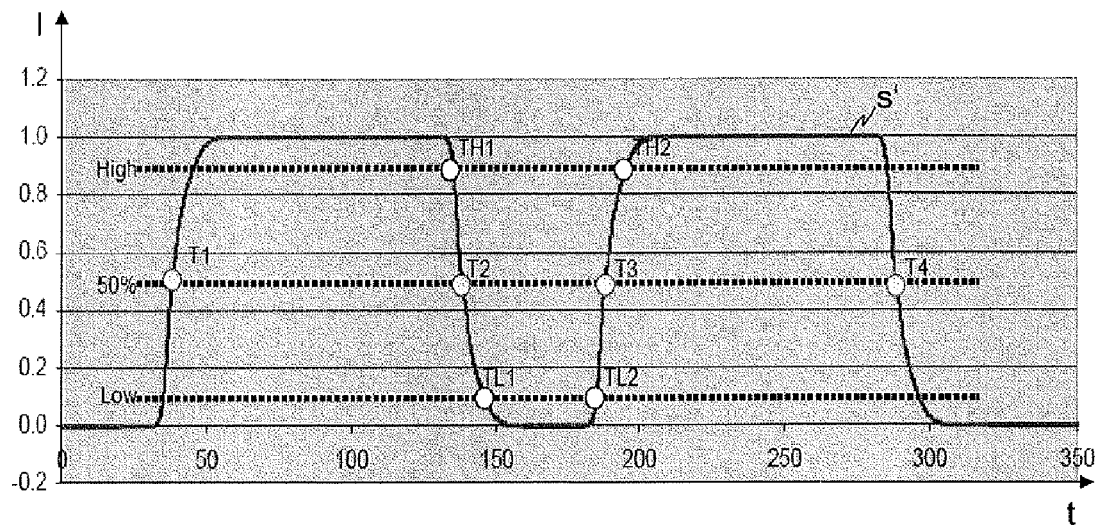
FIG. 6: shows a plurality of measurement points for determining time values in the measurement signal using the example of an offset-corrected measurement signal.

The processing system 5 establishes the beam width w (see FIG. 7) and, from this, the focus position on the basis of the evaluation of a signal drop or signal rise between two thresholds IH, IL for a high level and a low level of the signal level I in the case of a decreasing or increasing signal edge, which is created in the measurement signal s, s' when passing over an exit edge 312, 322 or entry edge 311, 321 of the measurement markings 3, 3a, 3b, 3c, 3d. The thresholds IH, IL for the high level and the low level are defined as part of the maximum level $I_{max}$, e.g. $IH=I_{max}(1-1/e^2)$ and $IL=I_{max}(1/e^2)$, as illustrated in FIG. 5 using the example of a decreasing signal edge. The time duration $\Delta t_1$ for the decreasing signal edge when passing over the exit edge 312, 322 emerges from the difference between the times TH1, TL1 for the time duration between reaching the high level IH and the low level IL of the signal level I when the exit edge 312 is passed over; $\Delta t_f=TL1-TH1$, as illustrated in FIG. 5. The time duration $\Delta t_r$ for the increasing signal edge when passing over the entry edge 321 emerges accordingly from the difference between the times TH2, TL2 (see FIG. 6) for the time duration between reaching the high level IH and the low level IL of the signal level I when the entry edge 321 is passed over; $\Delta t_r=TH2-TL2$.

Figure 7:
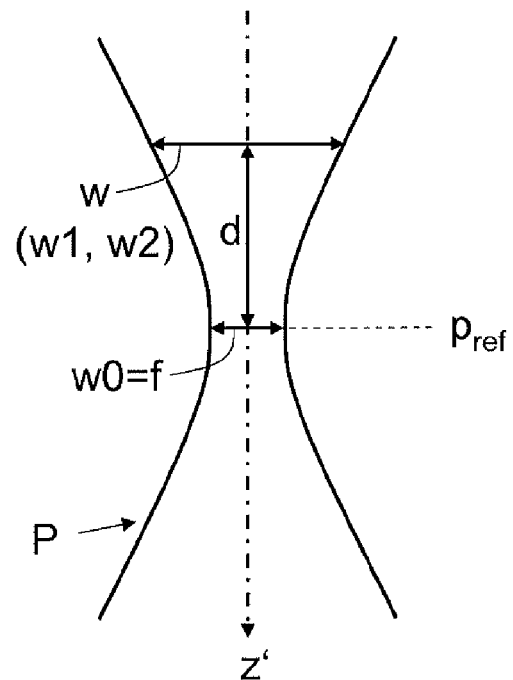
FIG. 7: shows a cross section of a laser beam with a Gaussian beam profile.

In the case of a constant scanning speed, it suffices to establish the time duration $\Delta t_f$, $\Delta t_r$ of a single signal edge in order to determine the reference position $P_{ref}$ of the focus F, i.e. the point of the projected laser beam 60a with the smallest beam width w0=f, (see FIG. 7). This reference position $P_{ref}$ corresponds to the position in the projection direction z' of the laser beam 60, 60a, in which the measured signal edge has the shortest time duration $\Delta t_f$, $\Delta t_r$. A focusing movement is required in order to find this reference position $p_{ref}$. Instead of establishing the time duration $\Delta t_1$, $\Delta t_r$ of the signal edge, the shortest, i.e. steepest, signal edge is determined in an alternative embodiment variant by differentiating the signal edge or by other signal processing methods (e.g. step response functions, signal width determination via the standard deviation and fitting a focusing function, etc.) and the corresponding position in the projection direction z' is captured as reference position $p_{ref}$. In one variant, a plurality of positions along the projection direction z' or projection axis z and associated beam widths w at these positions are stored in a table over an extended region, said beam widths determining the beam profile P (see FIG. 7) of the laser beam 60, 60a, which beam profile is defined in a beam profile table or as a Gaussian curve function.

The time $\Delta t_{ref}$ for passing over the gap 30 or bar of the measurement marking 3, 3a, 3b, 3c, 3d emerges from the difference of the times T2, T3 if the exit edge 312 and the entry edge 321 are passed over; $\Delta t_{ref}=T3-T2$, as illustrated in FIG. 4.

The processing system 5 establishes the time duration $\Delta t_1$ for the decreasing signal edge, the time duration $\Delta t_2$ for the increasing signal edge and the time $\Delta t_{ref}$ for passing over the gap 30 or bar with the defined width $d_{REF}$. The processing system 5 uses the defined width $d_{REF}$ and the determined time durations $\Delta t_1$, $\Delta t_2$ and $\Delta t_{ref}$ to establish the beam width w1 when passing over the exit edge 312 and the beam width w2 when passing over the entry edge 321 according to the following equations (1) and (2):

$$W1=(\Delta t_1/\Delta t_{ref})d_{REF} \quad (1)$$

$$W2=(\Delta t_2/\Delta t_{ref})d_{REF} \quad (2)$$

Here, $d_{REF}/\Delta t_{ref}$ corresponds to the current, local scanning speed when passing over the gap 30. The beam widths w1, w2 for example lie in the region between 1 µm and 10 µm. In the case of a constant scanning speed, the beam widths w1 and w2 have the same value. In the case of a changing scanning speed, particularly in the case of a linearly changing scanning speed, a mean value of the beam widths w1 and w2 is preferably formed, which is used for determining the focus position of the laser beam 60, 60a.

The determined beam widths w1, w2, in particular the mean value thereof, is used by the processing system 5 to establish the focus position of the laser beam 60, 60a on the basis of the known beam profile P of the laser beam 60, 60a, which, for example, is defined in the beam profile table or a corresponding Gaussian curve function. As can be seen in FIG. 7, the focus position of the laser beam 60, 60a is established from the distance d, given by the beam profile P, between the point in the beam profile P with the known beam width w, w1, w2 and the point $p_{ref}$ in the beam profile P at which the beam width w0 corresponds to the focus diameter f. If it is not possible a priori to ascertain in which direction the focus position $p_{ref}$ with the smallest beam width w0=f lies starting from the established beam width w, w1, w2, a second measurement is carried out with a modified focusing position (z-position). However, unlike in the case of confocal methods, there is no need for iterative, repeatedly adjusting focusing, in particular continuous focusing, during the measurement; two measurements are all that is required in this case.

As illustrated on the left-hand side in FIG. 3, a plurality of measurement markings 3a, 3b, 3c, 3d are arranged on the reference area 20 in one embodiment variant, with each of these measurement markings being embodied like the measurement marking 3 illustrated on the right-hand side in FIG. 3. The measurement markings 3a, 3b, 3c, 3d are arranged in a circle, preferably distributed uniformly around the circle, for example respectively at the intersection points of the circle with the ordinate y and abscissa x which run through the center of the circle. Here, the measurement markings 3a, 3b, 3c, 3d are respectively arranged on the circle such that the central axis r of the gap 30 of said respective marking runs through the center M of the circle. The edges 312, 321 delimiting the gap 30 therefore run substantially perpendicular to the circle. Moreover, the measurement markings 3a, 3b, 3c, 3d are aligned and oriented in the same direction—clockwise or anticlockwise—on the circle such that they are scanned by the laser beam 60, 60a on a (concentrically) circular (or spiral) scanning path 9, 9a, 9b, first over the entry region 31 thereof, thereafter over the gap 30 and then over the exit region 32 thereof in each case.

Depending on the radius of the circular (or spiral) scanning path 9, 9a, 9b, different time values T4, T4' emerge when passing over the oblique exit edge 322 with respect to the time values T2, T3 when passing over the upstream edges 312, 321, which delimit the gap 30. The greater the path radius is, the greater the time value T4, T4' will be when the wider side edge of the trapezoidal exit region 32 of the measurement markings 3, 3a, 3b, 3c, 3d is facing away from the center of the circle, as illustrated in FIG. 4 in a dashed fashion (and vice versa).

According to the equation below, the processing system 5 determines a centering characteristic ZK from the time values T2, T3, T4, T4', which centering characteristic specifies the relative radial position or centering of the circular or spiral scanning path 9 with respect to the circularly arranged measurement markings 3, 3a, 3b, 3c, 3d.

$$ZK=(T3-T2)/(T4-T3) \text{ or } ZK=(T3-T2)/(T4'-T3) \quad (3)$$

In the case of a complete revolution about the scanning path 9, 9a, 9b, the processing system 5 establishes and stores a centering characteristic ZK for each of the at least three measurement markings 3, 3a, 3b, 3c, 3d. The scanning path 9, 9a, 9b is centered in an optimum fashion with respect to the circular arrangement of the measurement markings 3, 3a, 3b, 3c, 3d when the centering characteristics ZK have the same value for all measurement markings 3, 3a, 3b, 3c, 3d. The centering is therefore independent of the local speed at which the laser beam 60, 60a or focal point F is moved on the scanning path 9, 9a, 9b, and of the absolute value of the path radius for as long as the latter lies in the region of the measurement markings 3, 3a, 3b, 3c, 3d. In a further embodiment variant, the processing system 5 moreover establishes the tilt of the reference area 20 with respect to the projection axis z or projection direction z' from the measurement values of a plurality of measurement markings 3, 3a, 3b, 3c, 3d.

In order to identify a quadrant, the processing system 5 establishes a quadrant marker QM as per the equation below:

$$QM=(T2-T1)/(T3-T2) \quad (4)$$

Here, in order to identify the quadrants or axes, the markings 3, 3a, 3b, 3c, 3d respectively have entry regions 31 with different dimensions, i.e. the entry regions 31 of the markings 3, 3a, 3b, 3c, 3d have different lengths in the scanning direction (distance between entry edge 311 and exit edge 312), which results in different time values T2-T1 and hence different values of the quadrant markers QM.

Finally, it should be noted that the shown and described signal profiles can also be inverted in the case of absorbing or complementarily embodied markings 3, 3a, 3b, 3c, 3d, with the described decreasing or increasing signal edges then being increasing or decreasing. Furthermore, it is noted that the shape of the signal edges depends on the beam profile and that the aforementioned description is directed to laser beams with a Gaussian beam profile. Laser beams with a non-Gaussian beam profile create signal edges with different shapes when scanning the marking edges. However, a person skilled in the art will understand that in cases where the signal-edge shape is not (e.g. analytically) known, the beam profile can be captured in a calibration step and the calculations can be adapted accordingly.

What is claimed is:

1. A method for determining the focus position of a laser beam in an ophthalmological laser projection system for projecting the laser beam along a beam path in a focused manner into eye tissue, comprising the steps of:
   arranging a reference area in said beam path of the ophthalmological laser projection system,
   projecting the laser beam from the ophthalmological laser projection system in a projection direction along said beam path,
   moving the laser beam by a scanner of the ophthalmological laser projection system along a scanning path and passing the laser beam along the scanning path over at least one measurement marking applied on the reference area arranged in the beam path, and creating a measurement signal when passing the laser beam along the scanning path over the measurement marking, the measurement signal having at least one signal edge created in the measurement signal when passing the laser beam along the scanning path over edges of the measurement marking,
   capturing the measurement signal created by and when passing the laser beam along the scanning path over the measurement marking,
   determining time values of the at least one signal edge created in the measurement signal when passing the laser beam along the scanning path over edges of the measurement marking, at least one time value corresponding to an upper signal threshold on the at least one signal edge and at least another time value corresponding to a lower signal threshold, the upper and the lower signal thresholds being lower than a maximum value and higher than a minimum value along the at least one signal edge, and
   establishing the focus position of the laser beam in the projection direction along said beam path of the ophthalmological laser projection system on the basis of the time values, wherein a time duration between the upper and the lower signal thresholds is determined, a beam width is determined on the basis of the time duration, and the focus position in the projection direction of the laser beam is established on the basis of the beam width.

2. The method of claim 1, wherein the measurement marking has a photoactive design, and the measurement marking creates the measurement signal when the laser beam passes over the measurement marking.

3. The method of claim 1, wherein the measurement marking has a reflecting or absorbing design, and the measurement signal is created as a result of a laser beam which is reflected or absorbed when the measurement marking is passed over.

4. The method of claim 1, wherein a beam width is determined on the basis of the time values, and the focus position in the projection direction of the laser beam is established on the basis of the beam width.

5. The method of claim 1, wherein the measurement marking is configured with a gap or bar having a known width, the gap or bar is passed over on a scanning path running across the gap or bar, a time duration for passing over the width of the gap or bar is determined from the measurement signal, and the focus position is established on the basis of this time duration and the width of the gap or bar.

6. The method of claim 1, wherein a plurality of measurement markings on the reference area are arranged in a circle, the measurement markings are respectively configured with at least one first edge running substantially perpendicular to the circle and a second edge running obliquely to this first edge, the circularly arranged measurement markings are passed over on a circular or spiral scanning path, time values are determined from the signal edges created in the measurement signal when passing over the first edge and the second edge, and a centering characteristic of the circular or spiral scanning path with respect to the circularly arranged measurement markings is established from the time values.

7. An ophthalmological laser projection system for projecting a laser beam in a projection direction along a beam path in a focused manner into eye tissue, comprising:
   a body arranged in said beam path and having a reference area and at least one measurement marking applied to the reference area,
   a scanner configured to move the laser beam along a scanning path and to pass the laser beam along the scanning path over at least one measurement marking applied on the reference area arranged in the beam path, creating a measurement signal when passing the laser beam along the scanning path over the measurement marking, the measurement signal having at least one signal edge created in the measurement signal when passing the laser beam along the scanning path over edges of the measurement marking,
   a detection system, which is configured to capture the measurement signal created by and when passing the laser beam along the scanning path over the at least one measurement marking, and
   a processing system, which is configured to determine time values of the at least one signal edge created in the measurement signal when passing the laser beam along the scanning path over edges of the measurement marking, and to establish a focus position of the laser beam in the projection direction along said beam path of the ophthalmological laser projection system on the basis of the time values, at least one time value corresponding to an upper signal threshold on the at least one signal edge and at least another time value corresponding to a lower signal threshold, the upper and the lower signal thresholds being lower than a maximum value and higher than a minimum value along the at least one signal edge, wherein a time duration between the upper and the lower signal thresholds is determined, a beam width is determined on the basis of the time duration, and the focus position in the projection direction of the laser beam is established on the basis of the beam width.

8. The device of claim 7, wherein the measurement marking has a photoactive design, and the detection system is configured to capture a measurement signal created by the measurement marking when passing over the measurement marking with the laser beam.

9. The device of claim 7, wherein the measurement marking has a reflecting or absorbing design, and the detection system is configured to capture the measurement signal on the basis of a laser beam reflected or absorbed when passing over the measurement marking.

10. The device of claim 7, wherein the processing system is configured to determine a beam width on the basis of the time values and to establish the focus position in the projection direction of the laser beam on the basis of the beam width.

11. The device of claim 7, wherein the measurement marking is configured with a gap or bar of a known width, the detection system is configured to capture a measurement signal created when passing over the gap or bar on a scanning path running across the gap or bar, and the processing system is configured to determine a time duration for passing over the width of the gap or bar from the measurement signal, and to establish the focus position on the basis of this time duration and the width of the gap or bar.

12. The device of claim 7, wherein a plurality of measurement markings on the reference area are arranged in a circle, the measurement markings are respectively configured with at least one first edge running substantially perpendicular to the circle and a second edge running obliquely to this first edge, the detection system is configured to capture a measurement signal created when passing over the circularly arranged measurement markings on a circular or spiral scanning path, and the processing system is configured to determine time values of the signal edges created in the measurement signal when passing over the first edge and the second edge, and to determine from the time values a centering characteristic of the circular or spiral scanning path with respect to the circularly arranged measurement markings.

* * * * *